United States Patent

Beckstein et al.

Patent Number: 5,382,894
Date of Patent: Jan. 17, 1995

[54] METHOD AND APPARATUS FOR THE MEASUREMENT OF CONTAMINANTS IN TEXTILES DURING CONTINUOUS PROCESSING

[75] Inventors: Hellmut Beckstein, Bad Abbach, Germany; Hans Bors, Fällanden/Zurich, Switzerland

[73] Assignee: Mahlo GmbH & Co. KG, Saal, Germany

[21] Appl. No.: 936,607

[22] Filed: Aug. 27, 1992

[30] Foreign Application Priority Data

Aug. 27, 1991 [DE] Germany ................ 4128344
Sep. 23, 1991 [DE] Germany ................ 4131616

[51] Int. Cl.$^6$ ............................................. G01N 27/00
[52] U.S. Cl. .................................. 324/71.1; 28/168; 68/19
[58] Field of Search ............ 8/147; 19/66 R; 28/165, 28/167, 168, 183; 68/18 R, 19, 158, 181 R; 73/61.44, 159, 160; 324/691, 693, 701, 71.1, 439

[56] References Cited

U.S. PATENT DOCUMENTS

| | | | |
|---|---|---|---|
| 3,986,274 | 10/1976 | Holm | 8/149.1 X |
| 4,269,047 | 5/1981 | Schuierer | 68/181 R |
| 4,373,362 | 2/1983 | Fleissner | 68/158 X |
| 5,063,646 | 11/1991 | Zeiffer et al. | 28/167 |
| 5,112,690 | 5/1992 | Cohen et al. | 428/411.1 |
| 5,195,225 | 3/1993 | Zeiffer et al. | 28/167 |
| 5,202,077 | 4/1993 | Marco et al. | 28/167 X |

FOREIGN PATENT DOCUMENTS

| | | |
|---|---|---|
| 68888 | 9/1969 | German Dem. Rep. |
| 223535A1 | 12/1985 | German Dem. Rep. |
| 249930A1 | 9/1987 | German Dem. Rep. |
| 2822214A1 | 11/1979 | Germany |
| 8914033.8U1 | 4/1990 | Germany |

OTHER PUBLICATIONS

"Sensoren in der Textilveredlungsindustrie", *Melliand Textilberichte* May 1990, pp. 365-370.

*Primary Examiner*—Walter E. Snow
*Assistant Examiner*—Christopher M. Tobin
*Attorney, Agent, or Firm*—Marshall, O'Toole, Gerstein, Murray & Borun

[57] ABSTRACT

When textile materials are treated with wet processes, attempts are usually made to detect organic and inorganic contaminant substances retained in the cloth either by allowing conductivity-measuring or other electrodes placed on the cloth to travel with it during transport, or by analyzing the fluid squeezed out of the cloth. The data obtained by these methods are extremely unreliable and subject to interfering factors. As a substantial improvement, it is proposed that the loading of the cloth with extraneous substances be measured in the interior of the cloth, between or at its surfaces. This can be achieved by applying and collecting solvent to extract samples of the extraneous substances from the cloth, section by section, and measuring the extraneous substances in the collected solvent quantitatively and/or qualitatively. Alternatively, the conductivity in the interior of the cloth, between its surfaces can be measured and used to determine the degree of contamination.

13 Claims, 1 Drawing Sheet

METHOD AND APPARATUS FOR THE MEASUREMENT OF CONTAMINANTS IN TEXTILES DURING CONTINUOUS PROCESSING

FIELD OF THE INVENTION

The present invention relates to a method and apparatus for the continuous measurement of ionic and non-ionic substances in textiles during continuous processing.

A fundamental problem with the wet stages of continuous textile processing, such as dyeing or high-grade finishing, is that these procedures can be detrimentally affected by residues left by preceding processes such as washing and, in some cases, acid treatment, squeezing, and drying. This can occur when the textile has been inadequately washed or the correct combination of washing and acidification, following NaOH processing, has not been employed. However, it is desirable to minimize the washing process for reasons of economy. For example, in the case of an acidic finishing process (cross-linking), residual acid in the textile can produce detrimental effects which actually damage the cloth. When the content of electrolyte or buffer is too high, or electrolyte and buffer are present in unfavorable proportions, the result may be interference with or complete inactivation of dyeing, printing or finishing.

DESCRIPTION OF THE PRIOR ART

In East German Patent Specification DD 223 535 A1 a method is described in which the electrical conductivity of a strip of cloth is measured between two roller electrodes and taken as a measure of the residual chemicals in the cloth. However, this procedure is of limited applicability because only a few of the extraneous substances in the cloth actually affect conductivity. Furthermore, even substances that are conductors in themselves can be adsorbed to the fiber surfaces and hence be inaccessible to the conductivity measurement.

East German Patent Specification DD 249 930 B1, describes a method wherein what is measured is not the conductivity at the surface of the cloth but rather the conductivity of the most recently used waste processing fluid which comprises a mixture of the processing fluid itself and the substances washed out of the cloth. Here, again, extraneous substances that do not contribute to electrical conductivity are not detected.

In East German Patent Specification DD-PS 68 888 there is described the chemical analysis not of the washing fluid recovered in the usual squeezing process but rather the fluid obtained in a special test squeezing following the quantitative squeezing of the cloth. This is because the substances contained in this fluid correspond more closely to those in the interior of the cloth. However, this known method is disadvantageous inasmuch as when the original squeezing process has removed all but a small amount of moisture it is very difficult to obtain samples by additional, even stronger squeezing, and the textile may even be damaged. Furthermore, even this method does not monitor the internal chemical state of the cloth.

SUMMARY OF THE INVENTION

The present invention is directed to the problem of further developing methods and apparatus of the kind described above in order to facilitate measurement of the extraneous substances in the squeezed cloth.

According to a first aspect of the present invention there is provided a method of measuring extraneous organic and inorganic substances in cloth treated by wet processes, wherein the measurement is carried out by means of an analyzer system after the cloth has been squeezed, and the quantity of extraneous substances present in the interior of the cloth between its surfaces are measured.

It will be appreciated that in the present invention, the extraneous substances at the surface of the cloth are not monitored but rather those contained in its interior, between the surfaces or in absorbed form. This can be achieved by extracting samples of the extraneous substances from sections of the cloth after squeezing, by applying and collecting solvent and analyzing the collected solvent quantitatively and/or qualitatively. It is important here that the solvent rinses out the interior of the cloth in particular and carries with it, at least in an exactly reproducible quantity, the extraneous substances present which can be in the residual water or another solvent, bound to the textile material, or dispersed in the cloth. The use of fresh solvent allows the "capture efficacy" of the contaminants to be considerably improved. It is also possible to enhance the capture efficacy considerably by using a special kind of solvent or solvent mixture, other than the solvent conventionally used in the washing bath.

Preferably, the amounts of solvent applied and collected and the amount of cloth to which it is applied are defined beforehand. Therefore both the application and the collection of the solvent are regulated according to the transport speed of the cloth to be tested. Thus the mean time during which the solvent is in contact with the cloth is simultaneously regulated or kept constant. The solvent is applied either substantially at a point or along a line, whereas it is collected over a greater transport distance.

Depending on the contaminants to be detected, it may be advantageous for the solvent to be applied as a vapor. In this case, as in the case of a liquid, the direction of application is more or less perpendicular to the surface of the cloth, so that the solvent is forced through the cloth. This ensures that the extraneous substances in the interior of the cloth, or fractions of them, are captured by the solvent. The capture efficacy can be adjusted by altering the temperature of the solvent, the volume flow and the strength of suction in the collecting device.

Alternatively, it is possible to measure the conductivity in the interior of the cloth, that is, not at its surfaces but between them. For this purpose electrodes can be inserted into the cloth, such as needle electrodes projecting from the surface of cylinders or wheels.

In order to monitor the extraneous substances that have no substantial influence on the conductivity of the cloth, it is advantageous to obtain experimental values for these substances and store them as a function of the measured conductivity. Surprisingly, tests have shown that when in one and the same process both substances that influence conductivity (especially ionic substances) and those that do not (e.g., nonionic substances or those with ions bound to the textile) are present, although there is no technique for measuring them simultaneously there is a specific relationship between the concentrations of the two kinds of substances, which can be measured experimentally. This relationship can be such that extraordinarily small conductivities, which, for instance, would not be detected according to the teaching of DD 223 535 A1, nevertheless serve as a significant indicator of intolerably high nonionic extraneous substances.

Thus according to a second aspect of the present invention there is provided an apparatus for implementing the method according to the first aspect, comprising first means mounted close to the cloth and capable of applying a solvent to the cloth; second means mounted close to the cloth and capable of collecting said solvent from the cloth; conveyor means for the solvent connected to said second means; and an analyzer arrangement to which solvent collected by said second means is transported by said conveyor means for analysis.

Preferably, the first means includes a heating unit to bring the solvent to a preset temperature or to evaporate it so that it reaches the cloth as a vapor.

Preferably also, solvent parameters such as its application pressure, volume flow and/or temperature are regulated, preferably in dependence on the speed with which the cloth is transported past the first and second means.

Preferably also, the solvent is collected over a longer distance (in the direction of transport of the cloth) than that over which it is applied to ensure that it is substantially removed and so that the mean period of time during which the solvent is in contact with the material is not negligible.

Alternatively, according to a second aspect of the present invention there is provided an apparatus for implementing the method according to the first aspect comprising first and second electrodes mounted in such a way that they can be brought into electrically conducting contact with the interior of said cloth to permit electrical resistance measurements to be taken, and an analyser arrangement capable of determining the conductivity of the cloth in its interior between its surfaces from said electrical resistance measurements.

These electrodes can, for example, include needles inserted into the cloth. Alternatively, or preferably in addition, needle-shaped electrodes are provided by means of which the redox potential, the concentration of H ions (pH) or of other ions (ion-sensitive electrodes) or the like can be measured.

Preferably also, the analyzer arrangement include a memory by means of which values representing the loading with extraneous substances (as memory contents) can be stored and read out in association with measured conductivity values (as addresses).

DESCRIPTION OF THE PREFERRED EMBODIMENTS

Figure 1:
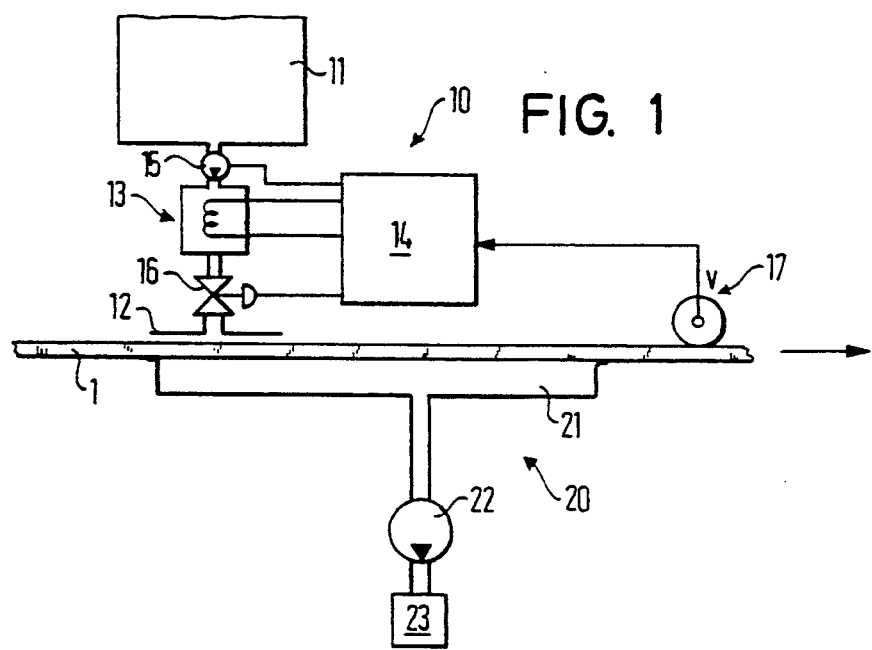
FIG. 1 is a schematic diagram of a first embodiment of apparatus according to the invention.

In the embodiment of the invention shown in FIG. 1, contaminants are extracted from the cloth by applying a solvent to it.

The cloth 1 is fed from squeezing equipment into a means 10 for solvent application and an associated means 20 for collection of the solvent.

The solvent-application means 10 includes a solvent container 11 out of which a solvent (e.g., water) is pumped by means of a solvent pump 15, through a heating unit 13 to an adjustable valve 16, which is set to control the volume flow, before passing through a nozzle 12 by means of which the solvent is pressed into the cloth. The nozzle 12 has a width of between 0.5 and 10 mm, and is preferably 2 mm. Its length is between 20 mm and 300 mm, and is preferably 150 mm. In addition, its horizontal orientation is preferably such as to ensure that the cloth travels past it without folding.

A controller 14 is provided, which controls the pump 15, the heating device 13 and the valve 16. These are regulated according to the speed v of the cloth 1, which can be monitored, for example by an appropriate synchro system 17.

On the side of the cloth strip 1 opposite the nozzle 12 is mounted a suction nozzle 21, through which the solvent applied to the cloth 1 is collected, and simultaneously condensed if necessary, by means of a pump 22 and conveyed to an analyzer system 23.

The suction nozzle 21 has a considerably enlarged opening, circa. 10–30%, over conventional nozzles of this type, and operates with a negative pressure in the range 0 to 200 mbar, preferably 80 mbar. To collect vaporized solvents, condensation devices (not shown) are provided.

The analyzer system 23 includes the sensors necessary for the analysis required such as pH- or ion-sensitive electrodes, conductivity sensors, flame photometer, gas chromatograph and the like.

The solvent, which includes a mixture of various solvents and in general also water, is applied at a temperature of between 25° C. and 170° C., preferably at 120° C., and at a flow rate such that the solvent volume exceeds the mass of the cloth from which the extraneous substances are to be extracted by a factor of between 2 to 50, preferably between 5 to 10.

The combination of the solvent-application and solvent-collecting devices shown in FIG. 1 can be fixed relative to the continuously transported cloth 1 or can be mounted movably so that it changes position across the direction of travel of the cloth (indicated by an arrow in FIG. 1). Such mobility allows analysis over the entire width of the cloth strip by an apparatus of relatively small size.

Figure 2:
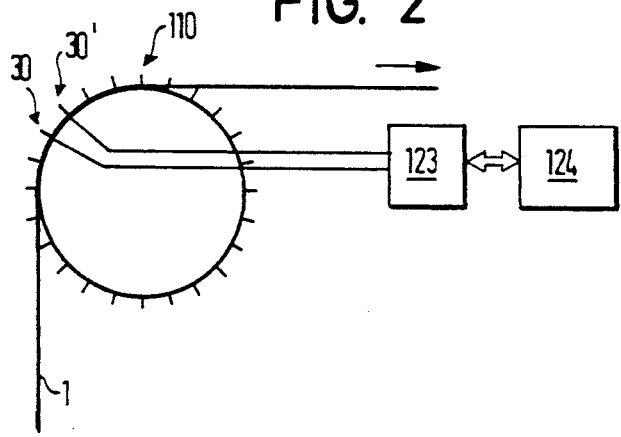
FIG. 2 is a schematic diagram of a second embodiment of the invention.

In a second embodiment of the invention shown in FIG. 2, the cloth 1 is penetrated by needle electrodes 30, 30' mounted on a rotating cylinder 110 over which the cloth 1 passes. By means of an analyzer 123, the resistance between these needles 30, 30' and thus the conductivity of the cloth is measured. These conductivity values in themselves provide a quantitative measure of some contaminants. For contaminants that have little or no influence on conductivity, a memory unit 124 is provided in which are stored values for these substances that have been obtained experimentally and stored using conductivity as a parameter.

Figure 3:
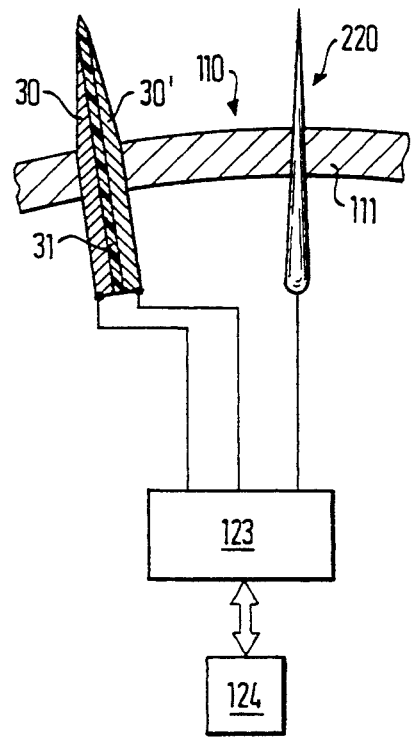
FIG. 3 is a part-sectional view of alternative electrode arrangement for use in the apparatus shown in FIG. 2.

In the modified arrangement shown in FIG. 3, the electrodes 30, 30' for measuring conductivity are combined with a dielectric 31 between them, in a single needle mounted in the wall 111 of the cylinder 110. With suitable dimensions, this arrangement allows the conductivity in the interior of a single fiber to be measured. The wall 111 of the cylinder 110 in the embodiment shown in FIG. 3 also bears needle-shaped ion-sensitive electrodes 220, with which the concentrations of H ions or other ions of interest within the cloth can be measured for analysis in the analyzer 123.

Preferably both methods, employing the apparatus shown in FIG. 1 and FIGS. 2/3, are used simultaneously, since it is generally necessary to measure electrical conductivity in any case.

The data obtained by the method in accordance with the invention can then be used, in particular, to regulate washing or neutralizing processes in a manner known per se.

What is claimed is:

1. A method of measuring extraneous organic and inorganic substances in a cloth treated by a wet process, comprising the steps of:
   squeezing the cloth;
   generating a vapor of solvent adapted for solving said extraneous organic and inorganic substances;
   applying said vapor to a predetermined area of said cloth in a direction perpendicular to a first surface of said cloth;
   controlling a volume flow of said vapor applied to said cloth;
   leaving said solvent in said cloth after application for a predetermined period of time;
   collecting said solvent from said cloth in a direction perpendicular to a second surface of said cloth opposite to said first surface for passing said solvent through said cloth and extracting said extraneous substances by said solvent from an interior of said cloth between said first and said second surface; and
   feeding said collected solvent to an analyzer system for measuring said extraneous substances extracted from said cloth by said solvent.

2. A method as claimed in claim 1, wherein said solvent comprises water and is applied at a temperature in the range between 25° C. and 170° C. inclusive.

3. A method as claimed in claim 2, wherein said solvent is applied at a temperature in the range between 115° C. and 125° C. inclusive.

4. A method as claimed in claim 1, wherein the volume flow of the solvent is controlled so as to depend on the mass of cloth from which the extraction is done.

5. A method as claimed in claim 4, wherein the volume flow of the solvent is controlled so as to depend on a travelling speed of cloth from which the extraction is done.

6. A method as claimed in claim 1, wherein the redox potential of said extraneous substances is measured.

7. A method as claimed in claim 1, wherein the concentration of hydrogen ions of said extraneous substances is measured.

8. A method as claimed in claim 1, wherein said extraneous substances are measured quantitatively.

9. A method as claimed in claim 1, wherein said extraneous substances are measured qualitatively.

10. An apparatus for measuring extraneous organic and inorganic substances in a cloth treated by a wet process comprising:
    squeezing means for squeezing liquid from said cloth being collected by said cloth during said wet process;
    vapor generating means for generating vapor of a solvent adapted for solving said extraneous organic and inorganic substances;
    vapor applying means comprising a first nozzle located upon a first surface of said cloth and having a defined nozzle cross-section for applying said vapor to an area of said cloth defined by said nozzle cross-section in a direction perpendicular to said first surface;
    control means for controlling a volume flow of said vapor applied to said cloth;
    collecting means including a second nozzle located upon a second surface of said cloth opposite to said first surface for collecting said solvent from said cloth in a direction perpendicular to said second surface through said cloth and for extracting said extraneous substances by said solvent from an interior of said cloth between said first and said second surface;
    analyzing means for measuring said extraneous substances extracted from said cloth by said solvent; and
    feeding means for feeding said solvent collected by said collecting means to said analyzing means.

11. An apparatus as claimed in claim 10, wherein said vapor generating means includes a heating unit to heat said solvent.

12. An apparatus as claimed in claim 10, wherein said control means includes at least one of pressure control means, volume flow control means and temperature control means for controlling at least one of pressure, volume flow and temperature of said solvent vapor.

13. An apparatus according to claim 10, in which said collecting means includes suction device means connected to said second nozzle and being adapted for retaining said solvent for a predetermined mean retention time in a continuously transported cloth.

* * * * *